US008186358B2

(12) United States Patent
Crivelli et al.

(10) Patent No.: US 8,186,358 B2
(45) Date of Patent: May 29, 2012

(54) SYSTEM AND METHOD FOR LOCATING AN INTERNAL DEVICE IN A CLOSED SYSTEM

(75) Inventors: Rocco Crivelli, Bellinzona (CH); Alec Ginggen, Plymouth, MA (US)

(73) Assignee: Codman Neuro Sciences Sárl, LeLocle (CH)

( * ) Notice: Subject to any disclaimer, the term of this patent is extended or adjusted under 35 U.S.C. 154(b) by 1749 days.

(21) Appl. No.: 11/193,228

(22) Filed: Jul. 29, 2005

(65) Prior Publication Data
US 2007/0027505 A1    Feb. 1, 2007

(51) Int. Cl.
*A61B 19/00* (2006.01)
*A61B 5/05* (2006.01)
(52) U.S. Cl. ........................................................ 128/899
(58) Field of Classification Search .......... 128/897–899; 600/424; 607/60
See application file for complete search history.

(56) References Cited

U.S. PATENT DOCUMENTS

| | | | |
|---|---|---|---|
| 4,102,344 A | 7/1978 | Conway et al. | |
| 4,114,601 A * | 9/1978 | Abels | 600/20 |
| 4,173,228 A | 11/1979 | Van Steenwyk et al. | |
| 4,804,054 A | 2/1989 | Howson et al. | |
| 4,905,698 A | 3/1990 | Strohl, Jr. et al. | |
| 5,099,845 A * | 3/1992 | Besz et al. | 600/424 |
| 5,171,228 A | 12/1992 | McDonald | |
| 5,211,165 A * | 5/1993 | Dumoulin et al. | 600/410 |
| 5,358,514 A | 10/1994 | Schulman et al. | |
| 5,375,596 A | 12/1994 | Twiss et al. | |
| 5,592,939 A * | 1/1997 | Martinelli | 600/424 |
| 5,683,432 A * | 11/1997 | Goedeke et al. | 607/32 |
| 5,713,939 A | 2/1998 | Nedungadi et al. | |
| 5,725,578 A | 3/1998 | Knapp et al. | |
| 5,727,552 A | 3/1998 | Ryan | |
| 5,941,251 A * | 8/1999 | Panescu et al. | 128/899 |
| 5,970,986 A * | 10/1999 | Bolz et al. | 128/899 |
| 6,009,878 A | 1/2000 | Weijand et al. | |
| 6,129,668 A * | 10/2000 | Haynor et al. | 600/424 |
| 6,233,476 B1 | 5/2001 | Strommer et al. | |
| 6,239,724 B1 * | 5/2001 | Doron et al. | 340/870.28 |
| 6,261,247 B1 * | 7/2001 | Ishikawa et al. | 600/587 |
| 6,305,381 B1 | 10/2001 | Weijand et al. | |
| 6,456,887 B1 * | 9/2002 | Dudding et al. | 607/60 |
| 6,474,341 B1 * | 11/2002 | Hunter et al. | 128/899 |
| 7,152,608 B2 * | 12/2006 | Hunter et al. | 128/899 |
| 7,191,013 B1 * | 3/2007 | Miranda et al. | 607/60 |
| 7,212,110 B1 * | 5/2007 | Martin et al. | 340/539.12 |
| 7,397,364 B2 * | 7/2008 | Govari | 340/539.12 |
| 7,528,094 B2 | 5/2009 | Blaha et al. | |
| 7,561,921 B2 | 7/2009 | Phillips et al. | |

(Continued)

*Primary Examiner* — John Lacyk
*Assistant Examiner* — Catherine E Burk
(74) *Attorney, Agent, or Firm* — Chery F. Cohen, LLC (57) ABSTRACT

A system and method for locating an internal device separated by a boundary from and in wireless communication with an external device. External device includes an active emitter mechanism wherein a carrier signal is modulated by a location interrogation signal thereby generating an external RF power signal during transmission to the internal device. A secondary antenna of the internal device receives the external RF power signal and induces an RF power signal therein that is converted to a DC induced voltage signal. An indication signal proportional to the intensity of the DC induced voltage signal induced in the secondary antenna is produced by the external device. The process is repeated each time the user moves the external device to a new location proximate the patient's body until a maximum DC induced voltage signal measurement is ascertained representative of a specific area in which the internal device is located.

31 Claims, 3 Drawing Sheets

U.S. PATENT DOCUMENTS

| | | |
|---|---|---|
| 7,565,197 B2 | 7/2009 | Howbrich et al. |
| 7,571,008 B2 | 8/2009 | Dinsmoor et al. |
| 7,574,266 B2 | 8/2009 | Dudding et al. |
| 7,610,099 B2 | 10/2009 | Almendinger et al. |
| 7,622,988 B2 | 11/2009 | Denison et al. |
| 7,631,415 B2 | 12/2009 | Phillips et al. |
| 7,635,541 B2 | 12/2009 | Scott et al. |
| 7,641,992 B2 | 1/2010 | Howard et al. |
| 7,642,013 B2 | 1/2010 | Howard et al. |
| 7,668,600 B2 | 2/2010 | Dudding et al. |
| 7,682,745 B2 | 3/2010 | Howard et al. |
| 7,699,060 B2 | 4/2010 | Behm |
| 7,711,433 B2 | 5/2010 | Davis et al. |
| 7,715,919 B2 | 5/2010 | Osorio et al. |
| 7,729,766 B2 | 6/2010 | Toy et al. |
| 7,738,951 B2 | 6/2010 | Rouw et al. |
| 7,761,167 B2 | 7/2010 | Bennett et al. |
| 7,815,602 B2 | 10/2010 | Mann et al. |
| 7,818,180 B2 | 10/2010 | Riff |
| 7,840,276 B2 | 11/2010 | Weispferring et al. |
| 7,848,819 B2 | 12/2010 | Goetz et al. |
| 2003/0208184 A1* | 11/2003 | Burke et al. ............... 604/891.1 |
| 2003/0229383 A1* | 12/2003 | Whitehurst et al. ............ 607/60 |
| 2006/0016452 A1* | 1/2006 | Goetz et al. .................... 128/899 |

\* cited by examiner

SYSTEM AND METHOD FOR LOCATING AN INTERNAL DEVICE IN A CLOSED SYSTEM

BACKGROUND OF THE INVENTION

1. Field of the Invention

The present invention is directed to a system and method for locating a device in a closed system hidden from visual observation by a boundary, and in particular, the invention is directed to a system and method for locating a medical device implanted in a human body.

2. Description of Related Art

In a closed system an electronic device is often implanted, disposed or positioned on one side relative to a boundary that prohibits the internal device from being visually observed. Over the course of time removal, maintenance or replacement of the internal device may be required for any number of reasons such as malfunction or depletion of its internal power source having a finite lifespan. In the medical application, implantable devices such as drug infusion pumps, sensors and stimulators, just to name a few, are gaining widespread use in treating a wide variety of medical conditions. Manufactures generally recommend that these implantable medical devices be mounted or sutured via one or more loops disposed along the exterior of the device so as to remain anchored in a substantially fixed location. It is not uncommon, however, for the surgeon to fail to suture the device in place during surgery or for the sutures to disengage permitting the implantable device to migrate through the body to a new location. Clearly determining the exact location of the device must be ascertained prior to or during surgery for its removal.

Even if removal is not necessary, locating the implantable medical device may be necessary to perform some type of maintenance on the device, for example, to replenish fluid (e.g., a drug reservoir) or drain fluid (e.g., drainage pump) therein. Drug infusion pumps are commonly implanted to dispense a medication, such as insulin or pain medication, from an internal supply reservoir via a catheter into the body. Once depleted of fluid, the reservoir must be refilled externally via insertion of a percutaneous needle through a septum covering a refill port. Several pumps feature a supplemental, auxiliary or second bolus port covered by a septum for receiving a bolus injection. A single dosage of fluid is dispensed via bolus injection into the bolus port versus a continuous infusion of medication stored in and dispensed from the internal supply reservoir via a catheter. The quantity or dosage of medication for replenishing the internal supply reservoir is typically greater than that dispensed by way of one time bolus injection. Accordingly, it is important to ensure selection of the correct injection site (e.g., refill port vs. bolus port) so that the patient is not inadvertently bolused with a reservoir refill volume of mediation. An overdose in medication via the inadvertent or accidental delivery of the refill supply reservoir quantity of fluid in a single dosage via the bolus port could result in adverse consequences, perhaps even death, to the patient.

Heretofore, locating the implantable drug infusion pump itself within the body has been realized through physical palpitation or manipulation. Once the position of the pump itself has been ascertained, it may be necessary to find the pump refill port or bolus port for injecting medication therein. The pump device is generally designed so that the refill and bolus ports are raised relative to the housing and thus susceptible to being identified by further physical palpitation or manipulation. However, as described above, it is imperative to the health of the patient that the pump refill port and bolus port be readily distinguished from one another prior to injection of the medication into the pump. For obvious reasons, the use of physical palpitation or manipulation alone to locate the raised port of interest is imprecise and subject to human error. Alternatively, or in combination with physical palpitation or manipulation, a pump specific template, typically provided by the manufacturer, may be positioned over the device, once it has been located, to precisely identify the intended port.

Such conventional methods and techniques are disadvantageous under certain circumstances. If the implantable device has dislodged from its original position and migrated through the body it may be difficult and time consuming to locate using only physical manipulation or palpitation. Especially in patients that are obese, physical palpitation and/or the use of templates are often impractical techniques for locating the device itself, much less the appropriate port.

A more sophisticated and precise approach as described in U.S. Pat. Nos. 6,305,381 and 6,009,878 employs an emitter on the implant side. An implant coil 22 is disposed around or beneath a septum 24. Instructions are received telemetrically by the implant to activate the implant coil 22. Energy is emitted from the coil and radiates therefrom. An implant location antenna array 103 including three antennas is moved externally along the patient's surface. Energy received by the implant location antenna array is detected by each of three antennas. It is presumed that the antennas are an equal distance away from the implant coil 22 and thus aligned with the septum when each of the antennas in the array are sensing the same amount of energy. This technique is problematic in that the emitter on the implant side consumes energy from the limited internal power source associated with the implantable medical device thereby shortening its lifespan.

U.S. Pat. No. 5,375,596 discloses an alternative method and apparatus for determining the position of catheters, tubes, placement guidewires and implantable ports within biological tissue. An external transmitter/detector unit 2 is positioned proximate the patient's skin and an antenna 14 emits an RF signal wherein the magnetic flux lines 36 project radially into the patient's body. The emitted RF field 36 is detected by an antenna of a device such as a catheter 30, 72 implanted internal to the body that is electrically connected to the external transmitter/detector unit 2 via a cable 16 and clip 18. In a particular application of the patented invention, a port access needle or infusion needle assembly 84 is employed to refill a reservoir of an implanted port assembly 64 with fluid to be dispensed through the body via a catheter 72. At the bottom of the internal cavity of the port body is a layer of conductive mesh 80 covered by a sealant layer 78. To determine the positioning of the catheter 72 an electrical connection must first be established between the external transmitter/detector unit 2 and the implanted port assembly 64. This is achieved by passing the needle through the sealant layer 78 so that it terminates with the conductive mesh 80 of the port body of the implant in order to complete the electrical connection. Requiring proper insertion of the needle into the port assembly as a preliminary step prior to locating the port itself defeats the underlying purpose of the present invention.

Moreover, this patented locating technique requires the use of a specialized or specific needle having a conductor exposed at each end. As disclosed in the patent, the conductive element disposed at the proximal end is adapted to be electrically coupled via a cable to the transmitter/detector 2 of the external device, while the exposed terminal end of the conductive element completes the electrical connection when properly inserted into the conductive mesh 80. Once the electrical connection has been completed (i.e., the exposed terminal end of the conductive element of the needle is properly inserted into the port so that it contacts the conductive mesh), antenna 14 of transmitter/detector 2 is passed over the surface of the patient's skin and RF field 36 radiates into the tissue of the patient. As that radiation is received by the antennas 32 in the catheter tube 34 a signal is conducted to the detector circuitry within transmitter/detector 2 by clip 18 and cable 16. By monitoring the signal from the catheter antenna 32, the location of the catheter may be determined. The physical wiring or cable link between the external transmitter/detector unit 2 and the internal device is also problematic in that there is always a high degree of risk of infection at the point of entry/exit through the skin.

It is therefore desirable to develop an improved system and method for locating a device disposed on one side of a closed system that solves the aforementioned problems associated with conventional devices.

SUMMARY OF THE INVENTION

The present invention solves the aforementioned problems associated with conventional location detection techniques.

An object of the invention is to develop a locating system that eliminates the need for an active emitter on the implant side by employing passive telemetry (i.e., emitter of RF power only outside of the body) so that less power is consumed by the internal device.

Another object of the present invention is to develop a locating system wherein no electrical connection need be established between the implant and the external device prior to locating the implant.

Yet another object of the present invention is to develop a universal location system that can be used with any conventional needle for refill or bolus injections.

Still another object of the invention is to develop a locating system that employs a wireless communication link between an external device and an implantable medical device, thereby eliminating the risk of infection at the point of entry/exit associated with wired connections passing through the patient's skin.

This invention relates to a system and method for locating an internal device separated by a boundary from and in wireless communication with an external device. The external device includes an active emitter mechanism wherein a carrier signal is modulated by a location interrogation signal thereby generating an external RF power signal during transmission to the internal device. A secondary antenna of the internal device receives the external RF power signal and induces an RF power signal therein that is converted to a DC induced voltage signal. An indication signal proportional to the intensity of the DC induced voltage signal induced in the secondary antenna is produced by the external device. The process is repeated each time the user moves the external device to a new location proximate the patient's body until a maximum DC induced voltage signal measurement is ascertained representative of a narrow area or region in which the internal device is located.

The present invention is directed to circuitry for locating an internal device in a closed system wherein the internal device is in wireless communication with and separated by a boundary from an external device. In accordance with the invention, the external device includes a first processor for generating a location interrogation signal, a first modulator for modulating a carrier signal by the location interrogation signal; and a first antenna for transmitting the modulated location interrogation signal including a substantially constant external RF power signal. On the opposite side of the boundary, the internal device includes: (i) a secondary antenna for receiving the modulated location interrogation signal including the external RF power signal from the external device and inducing an RF power signal therein; (ii) a converter for transforming the induced RF power signal to a DC induced voltage signal; (iii) a second processor for receiving as input the DC induced voltage signal and generating a location data signal including the DC induced voltage signal; and (iv) a second modulator for modulating the location data signal prior to wireless transmission by the secondary antenna from the internal device to the external device. The first processor of the external device receives as input the modulated location data signal from the internal device and, in turn, produces an indicator signal proportional to the intensity of the DC induced voltage signal induced in the secondary antenna of the internal device.

An alternative embodiment the indication signal in accordance with the present invention may be determined by comparing: (i) a first DC induced voltage signal representative of an amount of induced power received in the secondary antenna in response to a current interrogation location signal triggered by the external device and (ii) a second DC induced voltage signal corresponding to a previous interrogation location signal generated by the external device.

In addition, the invention also relates to a method for operating the system described above. Initially, the external device while positioned at a first location and in response to the selection or engagement by the user, technician, physician or nurse of a location button or key generates a location interrogation signal. A carrier signal is then modulated by the location interrogation signal. The external device transmits wirelessly via a primary antenna the modulated location interrogation signal including a substantially constant external RF power signal. On the opposite side of the boundary, the internal device detects an amount of RF power induced in a secondary antenna based on the substantially constant external RF power signal in the modulated location interrogation signal emitted by the primary antenna of the external device. The detected RF induced power is converted to a DC induced voltage signal. A processor produces a location data signal including the DC induced voltage signal. The location data signal is then wirelessly transmitted from the internal device to the external device. At the external device, the received location detection signal is demodulated to recover the DC induced voltage signal and an indicator signal is produced that is proportional (e.g., directly proportional or inversely proportional) to the intensity of the DC induced voltage signal in the secondary antenna of the internal device. Next the user, technician, physician or nurse positions the external device at a new location and the process is repeated. The internal device is located when the positioning of the external device produces a maximum DC induced voltage signal in the secondary antenna of the internal device.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

Figure 1:
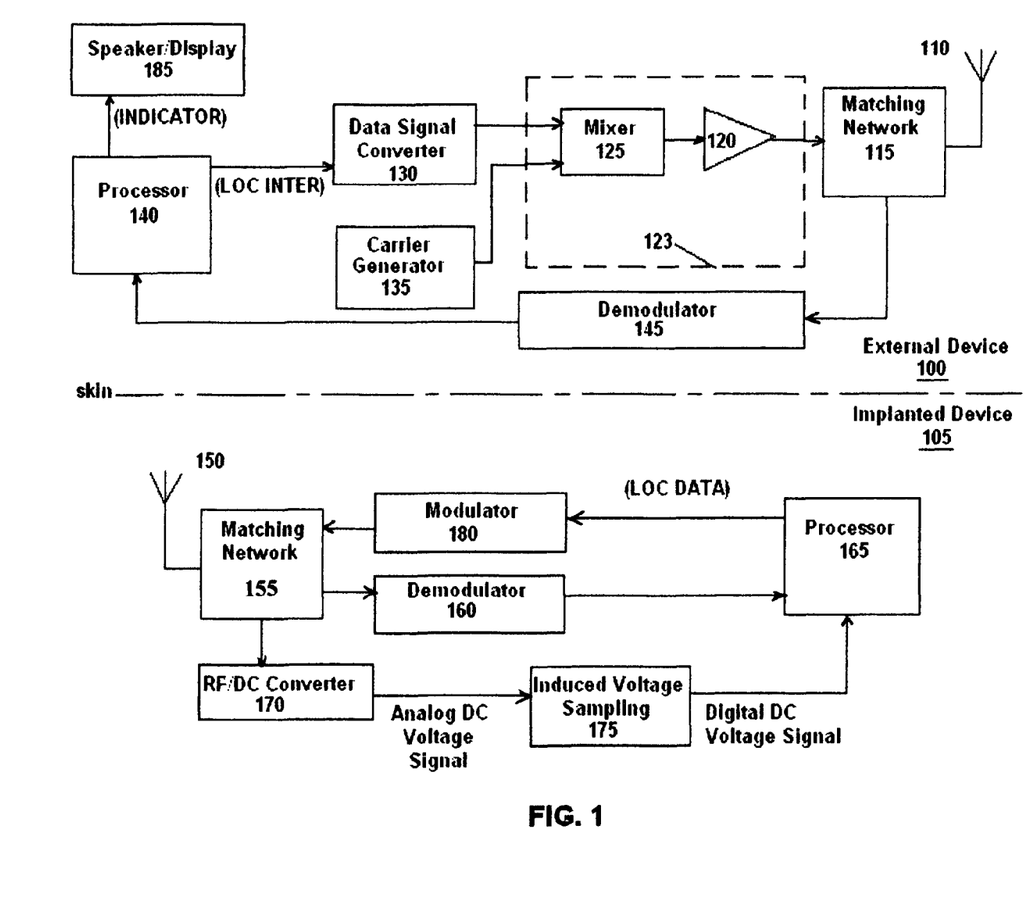
FIG. 1 is a schematic diagram of an exemplary implantable drug infusion pump closed system employing location detection circuitry in accordance with the present invention.

The present invention is directed to an apparatus in a closed system for locating an internal device hidden from visual observation by a boundary and in wireless communication with an external device. By way of example, an implantable medical system and method in accordance with the present invention is shown in FIG. 1 for an implantable drug infusion pump (e.g., an internal device) 105 in wireless communication with an external device 100, e.g., a control unit or PC. In a preferred embodiment, the implantable medical system is a transcutaneous energy transfer system (wireless energy transfer system or passive telemetry system) wherein the external device includes an active emitter for powering via externally radiated RF energy at least some circuitry of the internal device thereby extending the life span of the internal device. It is to be understood that the present invention may also be used for electronic systems not related to the medical field. Instead, the present invention is suitable for any system comprising an external device that communicates wirelessly across a boundary with a receiver of an internal device. The present invention advantageously eliminates the need for the internal device to have to employ an active emitter that would otherwise consume energy and reduce the lifespan of the internal device.

External device 100 includes a processor or controller 140 that in response to the user, physician, technician or nurse engaging or selecting a location key or button generates a location interrogation signal (LOC INTER) to be transmitted to the implantable medical device 105. The location interrogation signal induces a substantially constant level of RF power in a primary antenna 110 prior to transmission and may, but need not necessarily, include a data signal. A modulator 123 amplitude modulates the RF carrier wave by the location interrogation signal (LOC INTER) to produce an RF modulated location interrogation signal. In the embodiment shown in FIG. 1, the modulator 123 comprises a mixer 125 that receives as input the converted signal from block 130 and a carrier signal or wave from generator 135 to produce an RF modulated location interrogation signal. In a preferred embodiment the carrier signal or wave has a frequency of approximately 13.56 MHz. The output of mixer 125 is fed as input to a constant gain amplifier 120 and produces as output an RF amplitude modulated location interrogation signal. As an alternative embodiment, the arrangement of the mixer 125 and amplifier 120 may be switched. The RF amplitude modulated location interrogation signal is passed through a matching network 115 prior to being wirelessly transmitted via the primary coil, winding, or antenna 110 to the implantable medical device 105.

At the implantable medical device 105, the RF amplitude modulated location interrogation signal received by the secondary coil, winding, or antenna 150 is transmitted to a matching network 155. The RF amplitude modulated location interrogation signal transmitted by the external device 100 includes a substantially constant level of externally radiated RF energy and may, but need not necessarily, also include a data signal. At the output of the matching network 155, if the RF amplitude modulated location interrogation signal includes a data signal then it is demodulated by block 160 to extract the received data signal and convert into a data stream represented by logic levels able to be interpreted by the processor 165. In turn, the received data signal output from the demodulator 160 is transmitted to processor or controller 165.

A second output of the matching network 155 is electrically connected to an RF/DC converter 170 which collects the radiated RF energy from the received RF amplitude modulated location interrogation signal and converts it to an analog DC induced voltage signal. This induced power in the secondary coil 150 is sampled in block 175 to produce a digital DC induced voltage signal which is proportional (e.g., directly proportional or inversely proportional) to the induced power received in the implantable medical device 105. The DC induced voltage signal is preferably digital rather than analog so as to provide stable hardware that may be readily upgraded without changing the hardware itself and therefore is less expensive to manufacture and maintain. In a preferred embodiment, the power induced in the secondary coil 150 is sampled approximately once every tenth of a second. However, the sampling rate may be modified, as desired. Processor or controller 165 receives as a second input the digital DC induced voltage signal. In reply to the location interrogation signal from the external device 100 generated in response to the user, technician, nurse or physician selecting a location key or button, processor 165 in the implantable medical device 105 generates a responsive location data signal (LOC DATA) for wireless transmission back to the external device. The responsive location data signal (LOC DATA) comprises at least the digital DC induced voltage signal and may also include a responsive data stream signal. The responsive location data signal (LOC DATA) is received by modulator 180 which outputs the RF modulated responsive location data signal that is processed by the matching network 155 prior to being transmitted via the secondary coil 150 to the external device 100.

On the external device side, the RF modulated responsive location data signal (LOC DATA) transmitted by the implantable medical device 105 is received by the primary coil 110 and matching network 115. Demodulator 145 receives as input the RF modulated responsive location data signal (LOC DATA) output from the matching network 115 and converts it into a demodulated RF responsive location data signal represented by logic levels able to be interpreted by processor 140. Demodulated RF responsive location data signal includes at least the DC induced voltage signal representative of the amount of power received in the implantable medical device 105 in response to the interrogation location signal from the external device 100. Processor 140 receives as input the responsive location data signal (LOC DATA) output of demodulator 145 including the digital DC induced voltage signal representative of the amount of induced power received in the implantable medical device in response to the interrogation location signal (LOC INTER) from the external device 100.

Rather than an absolute value representing the precise distance separation between the antennas, in a preferred embodiment, processor 140 produces an indicator signal (INDICATOR) that is proportional (e.g., directly proportional or inversely proportional) to the intensity of the induced voltage in the secondary antenna 150 of the implantable medical device 105. Since no absolute value of distance separation between the external and internal devices is obtained, there is no need for pre-calibration. In turn, the indicator signal (INDICATOR) is transmitted to speaker/display 185 to produce an audible and/or visual signal representative of and proportional (e.g., directly proportional or inversely proportional) to the distance separation of the primary and secondary antennas 110, 150, respectively. It is well known in the art and thus need not be described in detail the circuitry for generating (i)

an audible frequency signal the frequency of which is proportional (e.g., directly proportional or inversely proportional) to the power induced/received in the secondary antenna of the implantable medical device to be applied to the speaker 185 in order to generate a tone or sound; or (ii) a visual indication signal representative of the relative power induced/received in the secondary antenna to be shown on a display 185 (e.g., using one or more LED or LCD).

In a first embodiment processor 140 receives the DC induced voltage signal transmitted by the implantable medical device 110 and, in turn, generates the indicator signal (INDICATOR) which is proportional (e.g., directly proportional or inversely proportional) to the intensity of the DC induced voltage signal and proportional (e.g., directly proportional or inversely proportional) to the distance separation between the primary antenna of the external device and the secondary antenna of the implantable medical device. As previously noted, the external device 100 emits a substantially constant amount of RF energy each time the user, technician, physician or nurse selects the location button or key. A direct correlation therefore exists among the distance separation between the antennas and the amount of power induced or received by the secondary antenna. The greater the separation distance between the primary and secondary antennas 110, 150, respectively, the smaller the amount of power induced or received by the secondary antenna 150 of the implantable medical device. On the other hand, as the distance separation between the antennas decreases, a larger amount of power is induced/received in the secondary antenna 150.

The intensity (e.g., number or level of visual bars, frequency and/or tone volume of audible sounds) of the indicator signal (INDICATOR) is proportional (e.g., directly proportional or inversely proportional) to the strength of the RF signal induced/received by the secondary antenna 150 in the implantable medical device. For example, as the primary antenna or coil 110 is brought closer to the secondary antenna or coil 150 a varying number of LEDs in an array are illuminated (e.g., in sequence as a bar graph), and extinguish sequentially as the primary antenna or coil 110 passes away from the secondary antenna or coil 150. Similarly, a speaker emits a tone whose frequency and/or volume varies as a function of the proximity of the primary antenna or coil 110 to the secondary antenna or coil 150. By way of example, as primary antenna 110 approaches the secondary antenna 150, the frequency or volume of the tone may increase, and as primary antenna 110 moves away from the secondary antenna 150 the frequency or volume of the tone may decrease, both in proportion to the proximity of the primary antenna 110 to the secondary antenna 150.

Thus, each time the external device 100 is moved or scanned over the body to a new location the process is repeated providing new information concerning the amount of RF energy received by the implant and thus adjusting the indication signal accordingly.

As an alternative embodiment, processor 140 may generate an indicator signal (INDICATOR) based on the comparison of: (i) a first DC induced voltage signal representative of the amount of induced power received in the implantable medical device in response to the current interrogation location signal triggered by the external device 100 and (ii) a second DC induced voltage signal corresponding to the previous interrogation location signal generated by the external device 100.

Figure 2:
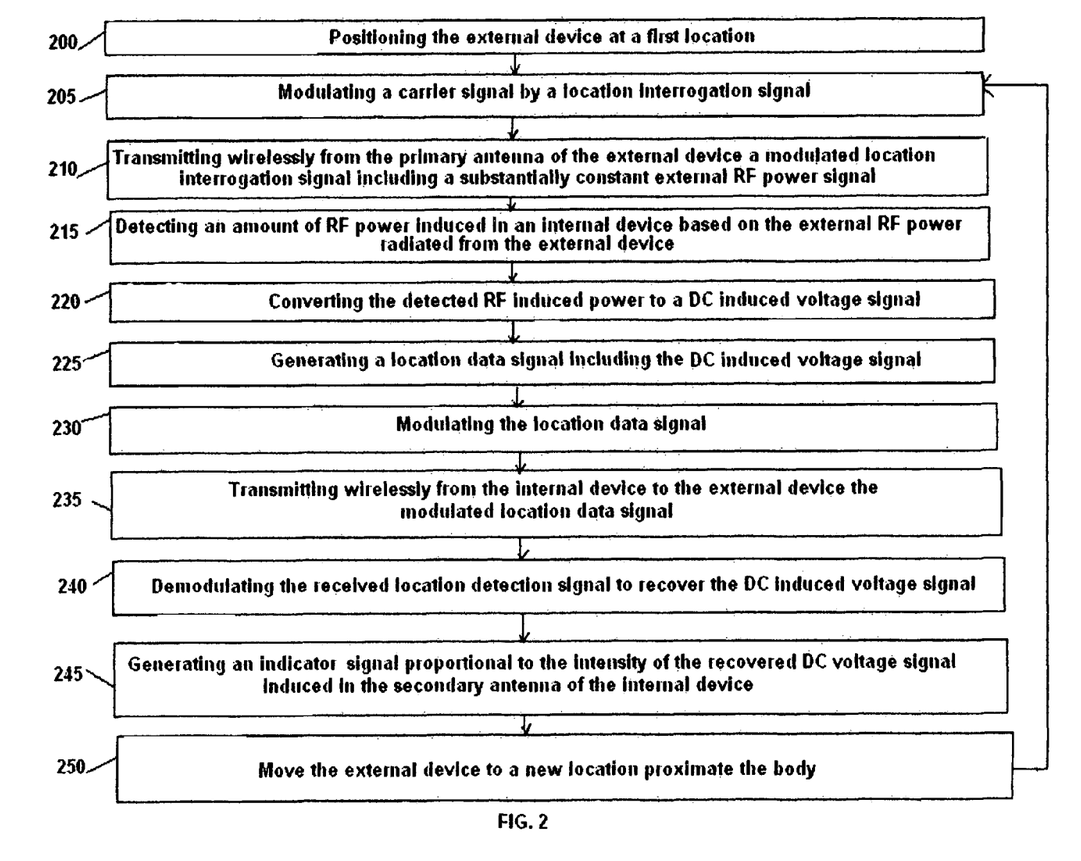
FIG. 2 is a flow chart of the operation of the location detection circuitry in accordance with the present invention.

FIG. 2 is a flow diagram of the process for locating an internal device in accordance with the present invention. Initially, in step 200, the external device 100 is positioned at a first location proximate the patient's body. In response to the user, technician, physician or nurse selecting or engaging a location button or key a location interrogation signal is generated. A carrier signal is modulated by the location interrogation signal in step 205. Thereafter, in step 210 the modulated location interrogation signal including a substantially constant external RF power signal is transmitted wirelessly from the primary antenna of the external device. An amount of RF power induced in the internal device is detected in step 215 based on the substantially constant external RF energy signal radiated from the external device. Thereafter, in step 220, the detected RF induced power is converted to a DC induced voltage signal. In step 225, a location data signal is generated by a processor, wherein the location data signal includes the DC induced voltage signal. The location data signal is modulated prior to being wirelessly transmitted back to the external device, as found in steps 230 and 235. On the external device side, the received location data signal is demodulated in step 240 to recover the DC voltage signal induced in the secondary antenna of the internal device (e.g., implantable medical device). In step 245, processor 140 generates an indicator signal proportional (e.g., directly proportional or inversely proportional) to the recovered DC voltage signal induced in the secondary antenna of the internal device. The user, physician, technician or nurse then moves the external device to a new location proximate the body, selects or engages the location key or button, and the process is repeated starting with step 205 until the location of the implant is ascertained by the detection of the maximum DC induced voltage signal in the secondary antenna. External device 100 will be at its closest position substantially atop of the internal device when the DC induced voltage signal received back by the external device is at a maximum, as represented by its corresponding indicator signal.

The process described above has been employed to locate the position of the internal device (e.g., implantable medical device) 105 itself. Once the internal device has been located, it is then possible to ascertain the exact or fine tuned location of the port of interest (e.g., bolus injection port versus refill injection port) via several conventional techniques. Hand manipulation of the skin and tissue surrounding the port may be used to locate the port of interest. Another approach as previously discussed is the use of a conventional manufacturer specific template placed over the implant once it has been identified in accordance with the present invention to locate the port of interest.

Figure 3:
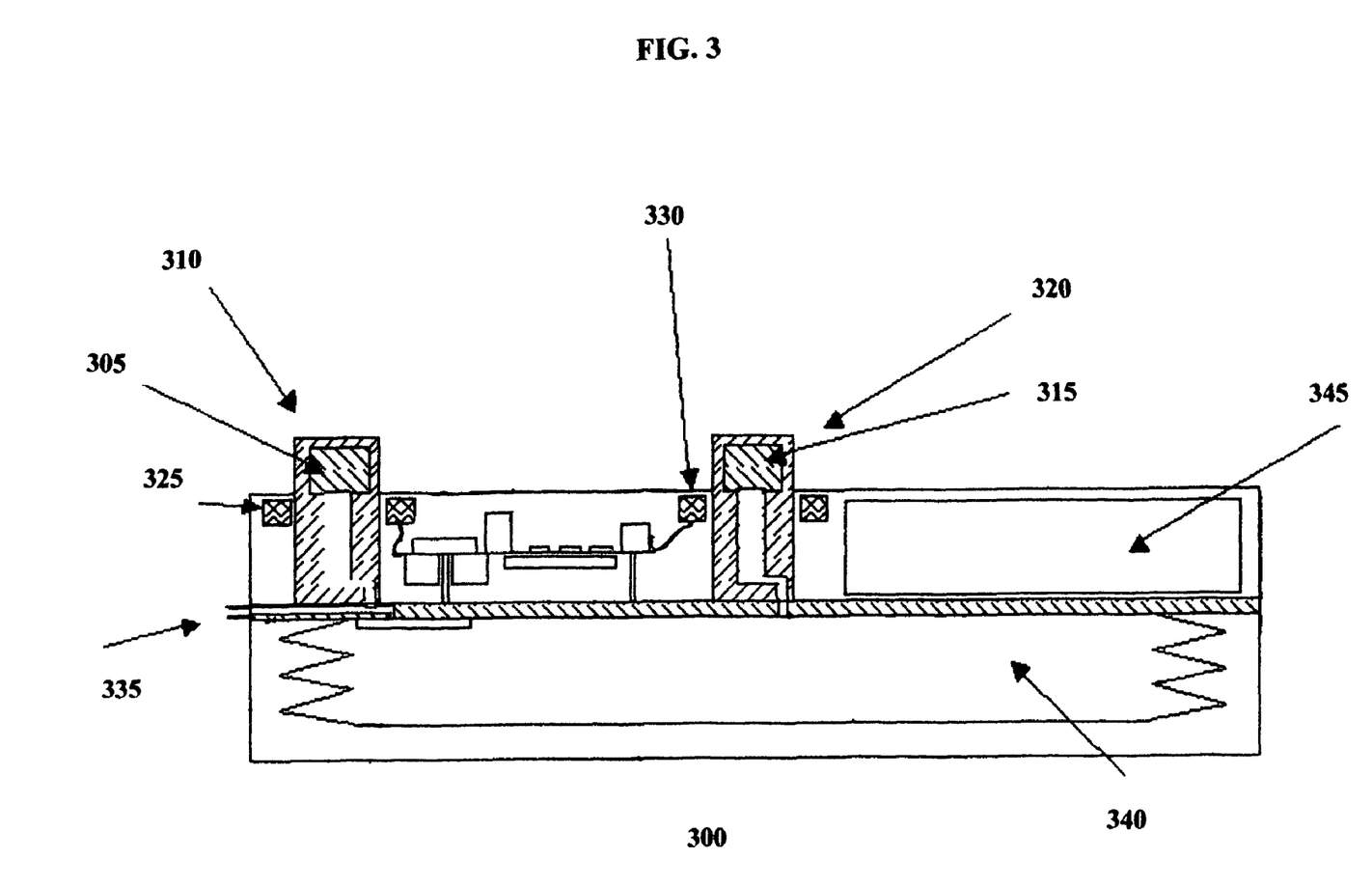
FIG. 3 is a cross-sectional view of an exemplary implantable drug infusion pump employing two separate antennas, one disposed proximate the bolus port and the other disposed proximate the refill port.

Alternatively, by positioning the secondary antenna 150 proximate one of the ports (e.g., the bolus port or the refill port) it is possible to simultaneously locate the implant 105 and the port of interest (e.g., bolus port versus refill port) using the wireless communication in accordance with the present invention. If the implant is designed with more than one port, then multiple antennas may be employed, one associated with and disposed proximate to each respective port. In the exemplary embodiment shown in FIG. 3, the implantable drug infusion pump 300 has a bolus port 310 with an associated bolus septum 305, a refill port 320 with an associated refill septum 315, a pump outlet 335, a drug chamber (bellows) 340, and a power source (battery) 345. A secondary antenna (bolus port location antenna) 325 is disposed proximate the bolus port 310 and a tertiary antenna (refill port location antenna) 330 is disposed proximate the refill port 320. The user, technician, physician or nurse selects either a bolus port location or a refill port location button or key on the external device 100. In response to either key being engaged, the external device 100 emits a substantially constant RF power that is received by the internal device and induces an RF power therein in the respective antenna, either secondary antenna 325 or tertiary antenna 330. The DC induced voltage signal representative of the RF power induced in the associated antenna of the internal device is transmitted wirelessly back to the external device. The ratio of the amount of substantially constant power emitted versus the amount of power induced in the antenna of interest (secondary or tertiary antenna) in the internal device may be used to identify the specific location of the port of interest.

Thus, the present inventive location detection circuitry determines the location of an internal device or the specific location of a particular feature of the internal device (e.g., port of interest) based on a ratio of the substantially constant power radiated from the external device to the DC voltage signal induced in the internal device and received back by the external device while at different positions relative to the internal device. The present inventive system is advantageous in that only the external device 100 has an active emission mechanism (i.e., a device that employs an active emitter so as to modulate the carrier wave by the data signal), whereas the internal device 105 has a passive emission mechanism (i.e., it does not employ an active emitter, instead varying the amplitude of the wave emitted by the control unit). Since the internal device does not employ an active emitter, instead relying on external RF energy emitted by the external device during transmission, the amount of energy consumed from the internal power source and used to power the internal device is minimized.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A closed system, comprising:
   an external device comprising:
      a first processor for generating a location interrogation signal;
      a first modulator for modulating a carrier signal by the location interrogation signal;
      a first antenna for transmitting the modulated location interrogation signal including a substantially constant external RF power signal;
   an internal device in wireless communication with the external device, the internal device comprising:
      a secondary antenna for receiving the modulated location interrogation signal including the external RF power signal from the external device and inducing an RF power signal therein;
      a converter for transforming the induced RF power signal to a DC induced voltage signal;
      a second processor for receiving as input the DC induced voltage signal and generating a location data signal including the DC induced voltage signal;
      a second modulator for modulating the location data signal prior to wireless transmission by the secondary antenna from the internal device to the external device; and
   the first processor receiving as input the modulated location data signal from the internal device and producing an indicator signal proportional to the intensity of the DC induced voltage signal induced in the secondary antenna of the internal device without calculating an absolute distance value.

2. The system in accordance with claim 1, wherein the internal device is an implantable medical device.

3. The system in accordance with claim 2, wherein the implantable medical device is an implantable drug infusion pump and the secondary antenna is disposed proximate a bolus port.

4. The system in accordance with claim 2, wherein the implantable medical device is an implantable drug infusion pump and the secondary antenna is disposed proximate a refill port.

5. The system in accordance with claim 4, further comprising a tertiary antenna disposed proximate a bolus port.

6. The system in accordance with claim 1, further comprising a speaker for generating an audible tone based on the indicator signal produced by the first processor.

7. The system in accordance with claim 1, further comprising a display for generating a visual display based on the indicator signal produced by the first processor.

8. The system in accordance with claim 1, wherein the internal device does not include an active emitter.

9. The system in accordance with claim 1, further comprising a sampler for receiving as input the DC voltage signal from the converter and producing a digital DC induced voltage signal.

10. The system in accordance with claim 1, wherein the indicator signal is directly proportional or inversely proportional to the intensity of the DC induced voltage signal induced in the secondary antenna of the internal device.

11. The system in accordance with claim 1, wherein intensity of the indicator signal is proportional to strength of the induced RF signal in the secondary antenna of the internal device.

12. The system in accordance with claim 1, wherein the external device has a single antenna.

13. A method for locating an internal device in a closed system including an external device in wireless communication with the internal device, the external device having an associated primary antenna and the internal device having an associated secondary antenna, comprising the steps of:
   (a) positioning the external device at a first location;
   (b) modulating a carrier signal by a location interrogation signal;
   (c) transmitting wirelessly from the primary antenna of the external device a modulated location interrogation signal including a substantially constant external RF power signal;
   (d) detecting an amount of RF power induced in the secondary antenna of the internal device based on the substantially constant external RF power signal in the modulated location interrogation signal emitted by the primary antenna of the external device;
   (e) converting the detected RF induced power to a DC induced voltage signal;
   (f) generating a location data signal including the DC induced voltage signal;
   (g) modulating the location data signal;

(h) transmitting wirelessly from the internal device to the external device the modulated location data signal;
(i) demodulating at the external device the modulated location data signal to recover the DC voltage signal;
(j) generating an indicator signal proportional to the intensity of the DC induced voltage signal in the secondary antenna of the internal device without calculating an absolute distance value; and
(k) positioning the external device at a new location, repeating the steps (b)-(j).

14. The method in accordance with claim 13, wherein the internal device is an implantable medical device.

15. The method in accordance with claim 14, wherein the implantable medical device is a drug infusion pump and the secondary antenna is disposed proximate a bolus port.

16. The method in accordance with claim 14, wherein the implantable medical device is a drug infusion pump and the secondary antenna is disposed proximate a refill port.

17. The method in accordance with claim 13, wherein prior to the step (d), selecting as the secondary antenna of the internal device from one of a bolus port antenna disposed proximate a bolus port and a refill port antenna disposed proximate the refill port to detect the amount of RF power induced therein.

18. The method in accordance with claim 13, wherein the internal device does not include an active emitter.

19. The method in accordance with claim 13, wherein the first location and the new location are both positioned proximate the patient's body.

20. The method in accordance with claim 13, wherein in step (j) the indicator signal is directly proportional or inversely proportional to the intensity of the DC induced voltage signal in the secondary antenna of the internal device.

21. The method in accordance with claim 13, wherein intensity of the indicator signal is proportional to strength of the induced RF signal in the secondary antenna of the internal device.

22. The method in accordance with claim 13, wherein the external device has a single antenna.

23. A closed system, comprising:
an external device comprising:
  a first processor for generating a location interrogation signal;
  a first modulator for modulating a carrier signal by the location interrogation signal;
  a first antenna for transmitting the modulated location interrogation signal including a substantially constant external RF power signal;
an internal device in wireless communication with the external device, the internal device comprising:
  a secondary antenna for receiving the external RF power signal from the external device and inducing an RF power signal therein;
  a converter for transforming the induced RF power signal to a DC induced voltage signal;
  a second processor for receiving as input the DC induced voltage signal and generating a location data signal including the DC induced voltage signal;
  a second modulator for modulating the location data signal prior to wireless transmission by the secondary antenna; and
the first processor receiving as input the location data signal from the internal device and producing an indicator signal device, without calculating an absolute distance value, based on the comparison of: (i) a first DC induced voltage signal representative of an amount of induced power received in the secondary antenna in response to a current modulated location interrogation signal triggered by the external device and (ii) a second DC induced voltage signal corresponding to a previous modulated location interrogation signal generated by the external device.

24. The system in accordance with claim 23, wherein the internal device does not include an active emitter.

25. The system in accordance with claim 23, wherein there is no need for pre-calibration.

26. The system in accordance with claim 23, wherein the carrier signal has a single frequency of approximately 13.56 MHz.

27. The system in accordance with claim 23, wherein intensity of the indicator signal is proportional to strength of the induced RF signal in the secondary antenna of the internal device.

28. A method for locating an internal device in a closed system including an external device in wireless communication with the internal device, the external device having an associated primary antenna and the internal device having an associated secondary antenna, comprising the steps of:
(a) positioning the external device at a first location;
(b) modulating a carrier signal by a location interrogation signal;
(c) transmitting wirelessly from the primary antenna of the external device a modulated location interrogation signal including a substantially constant external RF power signal;
(d) detecting an amount of RF power induced in the secondary antenna of the internal device based on the substantially constant external RF power signal in the modulated location interrogation signal emitted by the primary antenna of the external device;
(e) converting the detected RF induced power to a DC induced voltage signal;
(f) generating a location data signal including the DC induced voltage signal;
(g) modulating the location data signal;
(h) transmitting wirelessly from the internal device to the external device the modulated location data signal;
(i) demodulating at the external device the received location detection signal to recover the DC voltage signal;
(j) generating an indicator signal, without calculating an absolute distance value, based on the comparison of: (i) a first DC induced voltage signal representative of an amount of induced power received in the secondary antenna in response to a current modulated location interrogation signal triggered by the external device and (ii) a second DC induced voltage signal corresponding to a previous modulated location interrogation signal generated by the external device; and
(k) positioning the external device at a new location, repeating the steps (b)-(j).

29. The method in accordance with claim 28, wherein the internal device does not include an active emitter.

30. The method in accordance with claim 28, wherein there is no need for pre-calibration.

31. The method in accordance with claim 28, wherein intensity of the indicator signal is proportional to strength of the induced RF signal in the secondary antenna of the internal device.

* * * * *